(12) United States Patent
Favre et al.

(10) Patent No.: US 8,986,941 B2
(45) Date of Patent: Mar. 24, 2015

(54) PROCESS FOR MAKING A TRIGLYCERIDE COMPOSITION

(75) Inventors: Thomas Louis François Favre, Wormerveer (NL); Henry Kos, Wormerveer (NL); Krishnadath Bhaggan, Wormerveer (NL); Sylvain Jacques Fages, Orbe (CH)

(73) Assignee: Loders Croklaan B.V., Wormerveer (NL)

( * ) Notice: Subject to any disclaimer, the term of this patent is extended or adjusted under 35 U.S.C. 154(b) by 315 days.

(21) Appl. No.: 13/319,403

(22) PCT Filed: May 10, 2010

(86) PCT No.: PCT/EP2010/002865
§ 371 (c)(1),
(2), (4) Date: Nov. 8, 2011

(87) PCT Pub. No.: WO2010/130395
PCT Pub. Date: Nov. 18, 2010

(65) Prior Publication Data
US 2012/0052539 A1    Mar. 1, 2012

(30) Foreign Application Priority Data
May 11, 2009  (EP) .................................... 09251287

(51) Int. Cl.
| | |
|---|---|
| C12N 9/20 | (2006.01) |
| C12Q 1/61 | (2006.01) |
| C12P 7/64 | (2006.01) |
| A23G 1/38 | (2006.01) |
| C11C 3/08 | (2006.01) |
| A61K 38/00 | (2006.01) |

(52) U.S. Cl.
CPC ................ *C12P 7/6454* (2013.01); *A23G 1/38* (2013.01); *C11C 3/08* (2013.01)
USPC ............... 435/13; 435/71; 435/198; 435/183; 424/94.6; 426/35; 426/417

(58) Field of Classification Search
CPC ..................................... C11C 3/20; C11C 3/04
See application file for complete search history.

(56) References Cited

U.S. PATENT DOCUMENTS

| | | | |
|---|---|---|---|
| 4,268,527 A | | 5/1981 | Matsuo et al. |
| 4,863,865 A | * | 9/1989 | Franks ........................... 435/372 |
| 5,288,619 A | | 2/1994 | Brown et al. |
| 6,090,598 A | | 7/2000 | Yamaguchi et al. |
| 7,767,241 B2 | * | 8/2010 | Kuwabara et al. ............ 426/417 |
| 2007/0160739 A1 | * | 7/2007 | Kuwabara et al. ............ 426/607 |
| 2009/0123982 A1 | * | 5/2009 | Harris et al. ................... 435/134 |
| 2010/0222607 A1 | | 9/2010 | Arimoto et al. |

FOREIGN PATENT DOCUMENTS

| | | |
|---|---|---|
| EP | 0 245 076 A2 | 11/1987 |
| EP | 0 882 797 A2 | 12/1998 |
| JP | 06-327475 | 11/1994 |
| WO | WO 03/053152 A2 | 7/2003 |
| WO | WO 2007/029015 A1 | 3/2007 |
| WO | WO 2009/031680 A1 | 3/2009 |

OTHER PUBLICATIONS

Reference "Palm Mid FRaction" (2014, updated), http://onlinelibrary.wiley.com/doi/10.1002/(SICI)10970010(199608)71:4%3C483::AID-JSFA604%3E3.0.CO;2-8/abstract, p. 1.*
Samsudin et al. (1996) Use of Palm Mid-Fraction in White Chocolate Formulation, J. Sci. Food Agric., vol. 71, pp. 483-490.*
Abe, Ayumi et al., "*Rhizopus delemar* is the proper name for *Rhizopus oryzae* fumaric-malic acid producers," *Mycologia*, 99(5): 714-722 (Sep. 2007), XP002550657, Bisis Accession No. PREV200800139465.
Chi, Young Min, "Kinetic Study of the Lipase-Catalyzed Interesterification of Triolein and Stearic Acid in Nonpolar Media," *J. Biochem. Mol. Biol.*, 30(1):7-12 (Jan. 31, 1997), XP008113446.
Directive 2000/36/EC of The European Parliament and of the Council of Jun. 23, 2000 relating to cocoa and chocolate products intended for human consumption (OJ L 197, Mar. 8, 2000, p. 19), 10 pages.
Nakaya, Hideki et al., "Transesterification between triolelin and stearic acid catalyzed by lipase in $CO_2$ at various pressures," *Biotechnology Techniques*, 12(12): 881-884 (Dec. 1998).
Schmid, U. et al., "Highly Selective Synthesis of 1,3-Oleoyl-2-Palmitoylglycerol by Lipase Catalysis," *Biotechnology and Bioengineering*, 64(6): 678-684 (1999).
Seriburi, Vimon et al., "Enzymatic Transesterification of Triolein and Stearic Acid and Solid Fat Content of Their Products," *JAOCS*, 75(4): 511-516 (1998).
Notification of Transmittal of the International Search Report and the Written Opinion of the International Searching Authority for Int'l Application No. PCT/EP2010/002865; Date Mailed: Nov. 4, 2010.
Notification of Transmittal of the International Preliminary Report on Patentability for Int'l Application No. PCT/EP2010/002865; Date Mailed: Aug. 19, 2011.
European Search Report for European Application No. EP 09 25 1287; Date of Completion of Search: Oct. 16, 2009.

* cited by examiner

*Primary Examiner* — Maryam Monshipouri
*Assistant Examiner* — Samuel Liu
(74) *Attorney, Agent, or Firm* — Hamilton, Brook, Smith & Reynolds, P.C.

(57) ABSTRACT

A process for preparing a triglyceride composition comprising from 50 to 80% by weight StOSt and from 5 to 20% by weight StOO comprises reacting triolein with stearic acid in the presence of a 1,3-specific lipase from *Rhizopus oryzae* to form interesterified glycerides and fractionating the interesterified triglycerides.

9 Claims, No Drawings

PROCESS FOR MAKING A TRIGLYCERIDE COMPOSITION

This application is the U.S. National Stage of International Application No. PCT/EP2010/002865, filed May 10, 2010, which designates the U.S., published in English, and claims priority under 35 U.S.C. §§119 or 365(c) to EP Application No. 09251287.0, filed May 11, 2009.

This invention relates to a process for making a triglyceride composition and to the composition obtainable by the process.

Triglycerides comprise three fatty acid moieties bonded to a glycerol backbone. When a triglyceride contains two or more different fatty acid moieties, its properties, including its physical and chemical properties as well as physiological characteristics, may depend on the position on the glycerol backbone at which each of the fatty acids is attached in the molecule. Therefore, it can be desirable to control processes for producing triglycerides such that the different fatty acid residues are selectively attached at different positions on the glycerol backbone.

1,3-Distearoyl 2-oleoyl glyceride (also known as StOSt) is a valuable commercial product. For example, it may be used, either alone or together with other glycerides such as 1,3-dipalmitoyl 2-oleoyl glyceride, as a cocoa butter equivalent or substitute (CBE).

Shea butter is used commercially as a source of StOSt. Shea butter is obtained from the shea butter tree *Butyrospermum parkii*. Shea stearin, the higher melting fraction which is obtained by fractionation of shea butter, is enriched in StOSt but contains other triglycerides such as StOO and StLSt (where L represents linoleic acid). Thus, Shea stearin is used to produce cocoa butter equivalents (CBEs). The availability of Shea stearin is dependent on the supply of Shea nuts.

EP-A-0882797 relates to the preparation of a triglyceride having fatty acid residue A at the 1- and 3-positions and fatty acid residue B at the 2-position (ABA) symmetrical triglycerides from 2-monoglycerides using a 1,3-specific lipase.

U.S. Pat. No. 5,288,619 describes an enzymatic transesterification method for preparing a margarine oil having both low trans-acid and low intermediate chain fatty acid content. The method includes the steps of providing a transesterification reaction mixture containing a stearic acid source material and an edible liquid vegetable oil, transesterifying the stearic acid source material and the vegetable oil using a 1,3-positionally specific lipase, and then finally hydrogenating the fatty acid mixture to provide a recycle stearic acid source material for a recyclic reaction with the vegetable oil.

U.S. Pat. No. 4,268,527 discloses a method for producing a cocoa butter substitute (CBE) by transesterification of fats and oils containing glycerides rich in the oleyl moiety at the 2-position with an alcohol ester of stearic acid and/or palmitic acid in the presence of a lipase having reaction specificity to the 1,3-position of triglycerides and not more than 0.18% by weight of water based on the total weight of the reaction mixture. A cocoa butter substitute, rich in 1,3-distearyl-2-oleyl compound and 1-palmityl-2-oleyl-3-stearyl compound is said to be obtained.

EP-A-0245076 describes the preparation of edible fats by the reaction of high oleic sunflower oil with stearic acid in the presence of a lipase. The resulting composition, after wet fractionation, is significantly different from shea stearin in its StOSt and StOO contents.

Nakaya et al, Biotechnology Techniques, vol 12, no 12, 1998, 881-884 describes the transesterification reaction between triolein and stearic acid using an immobilised lipase from *Mucor miehei* in supercritical $CO_2$.

Seriburi et al, JAOCS, vol 75, no 4, 1998, 511-516 discloses the transesterification of triolein and stearic acid using lipases from *Rhizomucor miehei* or *Candida antarctica*.

U.S. Pat. No. 6,090,598 discloses an enzymatic process for interesterification of fats and oils using distillation. There is no disclosure of an example for producing StOSt and the only mention of the production of this triglyceride is starting from a stearic acid ester.

There remains a need for processes for the formation of StOSt triglycerides, in particular compositions that are similar to shea stearin in terms of the triglycerides that they contain. There is also a need for processes that do not involve the formation of undesirable side products that need to be removed from the product.

Accordingly, the present invention provides a process for preparing a triglyceride composition comprising from 50 to 80% by weight StOSt and from 5 to 20% by weight StOO, which process comprises reacting triolein with stearic acid in the presence of a 1,3-specific lipase from *Rhizopus oryzae* to form interesterified glycerides and fractionating the interesterified triglycerides.

Also provided by the invention is a triglyceride composition comprising from 50 to 80% by weight StOSt and up to 20% by weight StOO obtainable by the process of the invention.

It has surprisingly been found that it is possible to produce a triglyceride composition that is similar to shea stearin. This effect is achieved by using the 1,3-specific lipase from *Rhizopus oryzae* for the reaction of triolein with stearic acid and subsequently fractionating the product.

The reaction between triolein and stearic acid is typically carried out at a temperature of from 45 to 85° C. Preferably, the step of reacting the triolein with stearic acid is carried out at a temperature of from 65 to 80° C., more preferably from 65 to 75° C., even more preferably from 68 to 73° C. It has unexpectedly been found that surprisingly good results are obtained at these relatively higher reaction temperatures. It was surprising that the lipase retains sufficient activity at these high temperatures to catalyse the reaction effectively. The ability to carry out the reaction at these high temperatures permits the use of stearic acid as a starting material for the process rather than its esters which have lower melting points. This, in turn, means that the side products produced from the stearoyl esters during the reaction can be avoided.

The reaction of the triolein with the stearic acid is preferably carried out at atmospheric pressure i.e., in a non-pressurised system. The reaction may be carried out in a packed bed reactor. The reaction is preferably carried out as a continuous process.

The reaction of triolein with stearic acid is preferably carried out in the complete or substantial absence of added organic solvents, such as alcohols and/or ketones having from 1 to 6 carbon atoms. Typically, alcohols and/or ketones having from 1 to 6 carbon atoms will be absent from the reaction mixture or, if present, they will be present in an amount of less than 1% by weight, more preferably less than 0.5% by weight, such as less than 0.1% by weight, based on the weight of the reaction mixture.

The lipase that is used in the invention is from *Rhizopus oryzae*. The lipase may be produced in *Rhizopus oryzae* itself or produced recombinantly using a different host cell. The lipase may be modified, for example by the substitution or deletion of up to 10% of the amino acid residues in the enzyme (i.e., the lipase may have at least 90% identity with the wild type enzyme) without loss of lipase activity, but it is preferably the wild type enzyme. The lipase from *Rhizopus oryzae* is commercially available from Amano as Lipase D.

The lipase is preferably immobilised on a support. The support is preferably a polymer, more preferably a microporous polymer, such as a microporous polypropylene polymer (e.g., a homopolymer), for example as sold under the trade mark Accurel. The preferred loading of the lipase onto the support is in the range of from 0.1 to 25% by weight of enzyme based on the weight of the support, more preferably from 0.3 to 10% by weight, such as from 0.5 to 5% by weight. Theoretically (i.e., assuming the immobilisation has no effect on the activity of the enzyme), the activity of the immobilised enzyme (i.e., enzyme plus support) is preferably from 10,000 to 10,000,000 U/g, more preferably from 100,000 to 1,000,000 U/g. U represents lipase units determined by the standard assay for lipase activity, such as described in the examples below.

The immobilisation of the lipase on a support may be carried out using techniques known in the art. A preferred method of immobilizing the lipase on a support (such as a polymer e.g., polypropylene) is described in Schmid et al, "Highly selective synthesis of 1,3-oleoyl-2-palmitoylglycerol by lipase catalysis", Biotechnology and Bioengineering, 1999, vol. 64, no 6, pages 678-684.

Without wishing to be bound be theory, it is believed that the immobilisation of the enzyme on the support may contribute to the temperature stability of the lipase.

The reaction between triolein and stearic acid may be carried out on a continuous or batchwise basis. When the reaction is carried out batchwise, the weight ratio of supported enzyme to oil is preferably in the range of from 1:10 to 1:2000, more preferably from 1:20 to 1:1000.

The stearic acid that is used as a starting material for the process is in the form of a free acid (for example, it is not an ester). The stearic acid is typically relatively pure but less pure mixtures of fatty acids, for example having a stearic acid content of at least 70% by weight, more preferably at least 80% by weight, even more preferably at least 90% by weight, may also be used.

By using stearic acid rather than stearoyl esters as a starting material for the process, the formation of undesirable side products is avoided. For example, prior art processes that use esters of stearic acid, such as methyl stearate, liberate alcohols such as methanol during the process. This methanol must be removed from the product and so an additional step of distillation is then required. The present invention has as one of its advantages the possibility that distillation steps can be avoided or reduced in number.

The process of the invention is preferably free of undesirable alcohols such as methanol i.e., their maximum level in the reaction mixture during the process is preferably less than 1% by weight, more preferably less than 0.5% by weight, such as less than 0.1% by weight.

The triolein that is used as a starting material for the reaction may be relatively pure triolein or may be provided as a mixture of triolein with other glycerides, preferably comprising triolein in an amount of at least 40% by weight, such as at least 50% by weight. Preferably, the triolein is provided in the form of high oleic sunflower oil. It has been found that using this relatively inexpensive starting material provides a good product that is close in composition to shea stearin.

The weight ratio of stearic acid to the starting material comprising triolein is preferably in the range of from 1:1 to 1:2.

The reaction of the triolein with the stearic acid is typically carried out for a time of from 20 to 200 hours, more preferably from 30 to 150 hours.

After the triolein has been reacted with the stearic acid, the product is fractionated. Fractionation can be dry or wet but preferably the product is wet fractionated i.e., fractionated in the presence of a solvent. More preferably, the wet fractionation is carried out using acetone.

The fractionation process can involve one fractionation step or two or more fractionation steps at different temperatures.

Preferably, the reaction product is fractionated using acetone in a two-stage fractionation process. The fractionation temperature used for the first stage is preferably in the range of from 25° C. to 35° C., more preferably from 27° C. to 30° C. The fractionation temperature used for the second stage is preferably in the range of from 5° C. to 15° C., more preferably from 8° C. to 12° C. The weight ratio of oil to solvent in the wet fractionation step or steps is preferably in the range of from 1:3 to 1:7.

The process optionally includes further steps before or after fractionation. For example, the reaction product may be purified to some extent before fractionation. Preferably, however, the reaction product is removed from the lipase and then directly fractionated. After fractionation, the composition may be further fractionated, purified and/or refined.

Preferably, the process of the invention does not include a step of distillation.

The composition that is produced in the invention comprises from 50 to 80% by weight StOSt and from 5 to 20% by weight StOO. All percentages by weight of specific glycerides (e.g., StOSt, StOO, StLSt and StStSt) that are specified for the triglyceride composition are based on the total weight of triglycerides in the composition.

Preferably, the composition comprises from 60 to 80% by weight StOSt, even more preferably from 65 to 75% by weight StOSt.

The composition preferably comprises from 5 to 15% by weight StOO, more preferably from 8 to 12% by weight StOO.

The composition may also comprise StLSt. Preferably, the composition comprises from 2 to 8% by weight StLSt, such as from 3 to 5% by weight StLSt.

Typically, the composition will comprise StStSt. The composition typically comprises from 0.01 to 5% by weight StStSt, more preferably less than 2% by weight, such as from 0.1 to 1% by weight StStSt.

One preferred composition of the invention comprises:
(i) from 65 to 75% by weight StOSt;
(ii) from 5 to 15% by weight StOO;
(iii) from 2 to 8% by weight StLSt; and
(iv) from 0.01 to 5% by weight StStSt.

Another preferred composition of the invention comprises:
(i) from 60 to 80% by weight StOSt;
(ii) from 8 to 12% by weight StOO;
(iii) from 2 to 8% by weight StLSt; and
(iv) from 0.01 to 5% by weight StStSt.

Yet another composition of the invention comprises:
(i) from 65 to 75% by weight StOSt;
(ii) from 8 to 12% by weight StOO;
(iii) from 2 to 8% by weight StLSt; and
(iv) from 0.01 to 5% by weight StStSt.

The compositions of the invention will typically contain triglycerides other than StOSt, StOO, StLSt and StStSt and these will make up the balance of the triglycerides in the compositions to 100%.

Compositions of the invention may contain minor amounts, typically less than 20% by weight of the composition, of other components such as diglycerides, monoglycerides and free fatty acids (i.e., C12 to C24 saturated or unsaturated straight chain carboxylic acids). The compositions of the invention preferably comprise at least 80% by weight triglycerides, more preferably at least 90% by weight triglycerides, such as at least 95% by weight triglycerides.

Preferably, the triglyceride composition of the invention is blended with a palm mid-fraction (PMF) to obtain a CBE (cocoa butter equivalent). Preferably, the resulting blend is refined. The blends formed from compositions of the invention are particularly useful as replacements for cocoa butter in view of their melting profiles, as illustrated by their N values. The melting profiles are similar to that of a blend of shea stearin with PMF conventionally used as a CBE.

The blends may be used in any application in which cocoa butter is typically used. For example, the blends may be used in chocolate or chocolate-like products. The chocolate or chocolate-like products may be products in their own right, such as chocolate bars or pieces, or they may form part of another product such as a coating and/or inclusion for a confectionery or a bakery product or an ice cream. The chocolate or chocolate-like products will usually contain other ingredients such as, for example, one or more of cocoa powder, cocoa butter and sugar.

The following non-limiting examples illustrate the invention and do not limit its scope in any way. In the examples and throughout this specification, all percentages, parts and ratios are by weight unless indicated otherwise.

EXAMPLES

Assay Method for Lipase Activity

The activity of the lipase prior to immobilisation can be determined according to the following method.

A reaction mixture containing 5 ml of McLain buffer (pH 6.0, 0.1 M), 1 g of olive oil as substrate and 1 ml of lipase solution is incubated at 30° C. for 30 minutes with shaking (140 times oscillation per minute in 3 cm amplitude) in the presence of 30 glass beads of 5 mm diameter.

The reaction is stopped by the addition of 20 ml of acetone-ethanol (1:1) and the fatty acid released is titrated with 0.1 N KOH using phenolphthalein as indicator.

One unit (U) is defined as the amount of lipase which can release one micromole equivalent of fatty acid under the above conditions.

Examples 1 to 3

High oleic sunflower oil was reacted with stearic acid in the presence of a 1,3 specific lipase. The reaction was carried out in a continuous process (packed bed reactor) in which the acid to oil ratio used is 1.5. The reaction employed 1200 kg oil per kg of catalyst. The reaction is performed at 70° C. and the total reaction time was 50 to 100 hours. The throughput was adjusted based on the lipase used in order to obtain the highest conversion which is defined as follows:
Conversion (%)={([OOO]$_t$−[OOO]$_o$)+([OOO]$_{eq}$−[OOO]$_o$)}×100 wherein:
[OOO]$_t$=concentration of triolein in the oil at time t
[OOO]$_o$=concentration of triolein in the starting material
[OOO]$_{eq}$=concentration of triolein at equilibrium
The following three different lipases were used:

| Example | | Lipase |
|---|---|---|
| Example 1 | Invention | Lipase D* |
| Example 2 | Comparative | Lipozyme TL IM** |
| Example 3 | Comparative | Lipozyme RM IM*** |

*Rhizopus oryzae lipase from Amano immobilised on Accurel (for example, according to the method described in Schmid et al, Biotechnology and Bioengineering, 1999, vol. 64, no 6, pages 678-684)
**immobilised Thermomyces lanuginosa lipase from Novozymes A/S
***immobilised Rhizomucor miehei lipase from Novozymes A/S The reaction product was wet fractionated using acetone in a two-stage fractionation process. The fractionation temperature used for the first stage was about 28.5° C. and for the second stage 10° C. The oil to solvent ratio was 1:5. The stearin (higher melting fraction) was analysed and had the following composition:

| Triglyceride | Shea stearin | Example 1 | Example 2 | Example 3 |
|---|---|---|---|---|
| StStSt | 1.5 | 0.5 | 0.6 | 2.3 |
| StOSt | 71.9 | 70.9 | 40.7 | 39.5 |
| StOO | 5.0 | 9.7 | 24.7 | 28.9 |
| StLSt | 6.2 | 4.2 | 2.3 | 2.2 |
| Others | To 100 | To 100 | To 100 | To 100 |
| Yield (%) | | 38 | 37 | 48 |

The results show that the composition produced according to the invention closely resembles shea stearin.

Example 4

The stearin fractions obtained in Examples 1 to 3 were blended with palm mid-fraction (PMF) to produce a cocoa butter equivalent (CBE). The solid fat contents were determined and the following results were obtained:

| Solid Fat Content | Blend with Shea stearin | Example 1 | Example 2 | Example 3 |
|---|---|---|---|---|
| N20 | 68-79 | 72.1 | 60.9 | 62.9 |
| N25 | 56-68 | 63.6 | 35.5 | 43.6 |
| N30 | 42-53 | 47.0 | — | 20.1 |
| N35 | <5 | 1.6 | — | 2.4 |
| N40 | <1 | 0 | — | 0.5 |

The N30, N35 and N40 values for the blend with Example 2 are not yet available.

The results show that the blend formed from Example 1 according to the invention most closely resembles a blend with Shea stearin in terms of its melting profile and so constitutes the best CBE.

The invention claimed is:

1. A process for preparing a triglyceride composition comprising from 50 to 80% by weight 1,3-distearoyl 2-oleoyl glyceride (StOSt) and from 5 to 20% by weight 1-stearoyl 2,3-dioleoyl glyceride (StOO), which process comprises directly reacting triolein with stearic acid at a temperature of from 68 to 73° C. in the presence of a 1,3-specific lipase from Rhizopus oryzae to form interesterified triglycerides and fractionating the interesterified triglycerides wherein said direct reaction is carried out in the complete absence of alcohols and wherein the lipase retains sufficient activity at said temperatures to catalyze the reaction effectively.

2. Process as claimed in claim 1, wherein the triolein is provided as high oleic sunflower oil.

3. Process as claimed in claim 2, wherein the fractionation is carried out by wet fractionation using acetone.

4. Process as claimed in claim 3, wherein the lipase is immobilised on a support.

5. Process as claimed in claim 4, wherein the composition comprises from 60 to 80% by weight StOSt.

6. Process as claimed in claim 5, wherein the composition comprises from 5 to 15% by weight StOO.

7. Process as claimed in claim 6, wherein the composition comprises from 2 to 8% by weight 1,3-distearoyl 2-linoleoyl glyceride (StLSt).

8. Process as claimed in claim 1 which further comprises forming a blend by blending the triglyceride composition with palm mid-fraction.

9. Process as claimed in claim 8, wherein the blend is refined.

* * * * *